United States Patent [19]

Kallick

[11] 4,329,331
[45] May 11, 1982

[54] DIAGNOSTIC METHOD FOR DETECTION OF SYSTEMIC LUPUS ERYTHEMATOSUS

[76] Inventor: Charles A. Kallick, 181 W. 135 St., Lemont, Ill. 60439

[21] Appl. No.: 129,895

[22] Filed: Mar. 13, 1980

[51] Int. Cl.³ .................. G01N 33/54; G01N 33/58; C12Q 1/00; C12R 1/90
[52] U.S. Cl. .................................. 424/8; 23/230 B; 422/57; 424/12; 424/85; 424/88; 435/4; 435/7; 435/30; 435/258; 435/947
[58] Field of Search .............. 424/7, 8, 12, 85, 88; 23/230 B; 435/4, 6, 7, 30, 258, 947; 422/57

[56] References Cited

PUBLICATIONS

Kallick, Arth. and Rheum., vol. 23, Feb. 1980, pp. 197–205.
Kallick, Nature, New Biol., vol. 236, Apr. 5, 1972, pp. 145–146.

*Primary Examiner*—Anna P. Fagelson
*Attorney, Agent, or Firm*—Dressler, Goldsmith, Shore, Sutker & Milnamow, Ltd.

[57] ABSTRACT

Systemic lupus erythematosus is diagnosed by contacting the blood serum of a patient with anaplasma antigen derived from a vertebrate infected by an organism of the genus Anaplasmataceae and thereafter contacting the antigen with an indicator for human immunoglobulin components.

8 Claims, No Drawings

DIAGNOSTIC METHOD FOR DETECTION OF SYSTEMIC LUPUS ERYTHEMATOSUS

DESCRIPTION

1. Technical Field of the Invention

This invention relates to disease detection, and particularly to a method for diagnosis and detection of systemic lupus erythematosus.

2. Background of the Invention

Lupus erythematosus is a disease which is more prevalent than is generally recognized. Discoid lupus erythematosus, which affects the skin, is generally recognized by its particular type of skin rash, although mild cases are frequently unrecognized. Systemic lupus erythematosus (hereinafter SLE), which may or may not be associated with skin lesions, may be associated with joint pains resembling those of arthritis, or may be associated with other symptoms or conditions, such as pleurisy, anemia or kidney involvement.

With symptoms so varied, it is understandable that SLE is frequently misdiagnosed and unrecognized.

The unifying factor which identifies such varying symptoms as manifestations of a single disease, SLE, is the presence, in the blood of the patients, of the unique lupus erythematosus (or LE) cell. However, not all patients with an active SLE condition exhibit a positive LE cell test when they are first checked. It may take repeated tests over a period of several years before some SLE patients have a positive LE cell test.

In essence, the LE cell test involves the microscopic examination of blood cell smears to discern colors and shapes associated with certain leukocyte cells, rosettes, hematoxylin bodies and rouleaux formations. The cells are first isolated in the buffy layer of centrifuged, macerated, clotted, venous blood, then smeared on a glass plate, stained with Wright's stain, and dried.

Diagnosis of SLE through the LE cell test is difficult because there are other leukocyte cell conditions which resemble the LE cell. It requires the services of an experienced hematologist; and repeated tests with negative results over a period of time are sometimes necessary before an SLE condition can be ruled out.

More recently, diagnostic tests for SLE have been devised which utilize desoxynucleic acid (DNA) antibodies, or antinuclear (ANA) antibodies for detection of the condition. These tests seem to correlate slightly better than the LE cell test to the SLE condition and have been accepted as associated with SLE. However, a significant percentage of SLE patients do not have positive tests by these methods throughout the course of their illness. In addition, positive DNA and ANA antibodies are found in many patients who do not have SLE. The diagnosis of SLE through the LE cell test, or through DNA or ANA antibodies, is difficult because no Lupus patient seems to respond to a single definitive test, or profile of tests, which is invariably positive.

SUMMARY OF THE INVENTION

In accordance with the present invention, a method is provided for determining the presence of systemic lupus erythematosus in a patient which comprises contacting blood serum from said patient with anaplasma antigen derived from a vertebrate infected with an organism of the genus Anaplasmataceae, and thereafter contacting said antigen with an indicator for human immunoglobulin components.

Organisms of the genus Anaplasmataceae are rickettsia-like agents which cause hypergammaglobulinemia, Coomb's positive hemolytic anemia, and erythrocyte hemagglutinins in almost all species of vertebrates studied. The organisms are arthropod borne, vary markedly in geographic distribution, are highly species specific and have not been reproducibly cultivated outside the living host. The genus includes haemobartonella, eperythrozoon and anaplasma.

Kallick et al., in an article entitled "Systemic Lupus Erythematosus Associated with Haemobartonella-like Organisms" (Nature New Biology, Vol. 236, No. 66, pp. 145–146, Apr. 5, 1972) disclosed the presence of structures, identified by morphology as haemobartonella-like, on erythrocytes of patients diagnosed as having SLE. Blood films from eight patients with diagnosed SLE, when stained with acridine orange, all showed regularly occurring round bodies 0.3 to 0.5 m in diameter on and in the erythrocytes. Blood films from fourteen individuals constituting a control group showed such structures in only one of the individuals when the films were studied by one examiner and in only two of the individuals when the films were studied by another examiner.

In addition, the erythrocytes of four of the eight SLE patients showed fluorescence in the presence of fluorescein-conjugated Immunoglobulin G (Ig G) from animals convalescent to infection by *E. suis* and *A. marginale*. In contrast, no such fluorescence was observed in the erythrocytes of any of the control group under similar conditions.

The direct association of human erythrocytes with antibodies from an infected animal does not provide a reliable indicator of SLE infection. The method of the present invention utilizes the more sensitive association of antibodies from the suspected SLE patient and erythrocytes from an infected animal. More specifically, the present invention provides a method for determining the presence of systemic lupus erythematosus in a patient which comprises contacting blood serum from said patient with anaplasma antigen derived from a vertebrate infected with an organism of the genus Anaplasmataceae, and thereafter contacting said antigen with an indicator for human immunoglobulin components.

Anaplasma Antigen (AA) may be prepared by methods known in the art, such as by the method described by Ristic in an article entitled "A Capillary Tube Agglutination Test for Anaplasmosis-A Preliminary Report" (J. Am. Vet. Med. Assoc. 141:588–594, 1962). As prepared in the manner described, the material represents concentrated marginal bodies of *Anaplasma marginale* with an obligatory component of bovine erythrocyte stroma.

The indicator for human immunoglobulin components is preferably an antihuman gammaglobulin, obtained from a mammal injected with human gammaglobulin, conjugated with a detectable molecule or fragment. The preferred indicator is goat-derived antihuman gammaglobulin conjugated with fluorescein. If desired, a radioactive conjugation material may be used in place of the fluorescein.

In a typical diagnostic test for systemic lupus erythematosus, Anaplasma antigen slides are first prepared by smearing, on glass slides, harvested erythrocytes from a cow infected with *Anaplasma marginale*. The smears are fixed in absolute ethanol for 10 seconds and then maintained at $-70°$ C.

The AM slides are overlaid with various dilutions of serum from the suspected patient, incubated at 37° C. for 30 minutes, then rinsed twice for two minutes each time in phosphate buffered saline solution (PBS) at a pH of 7.4 at room temperature, then air dried.

The slides are then overlaid with normal goat serum (1:10), incubated, washed and dried. Finally, the slides are stained with goat-derived antihuman gammaglobulin conjugated with fluorescein isothiocyanate (FITC).

With appropriate controls (described below) fluorescence in the bovine erythrocytes on the slides, particularly at high titers, indicates the presence of AM antibodies in the serum of the patient and a strong likelihood that the patient has SLE.

DETAILED DESCRIPTION OF THE INVENTION

In a test of the method of this invention, Anaplasma antigen (AA) was prepared by the method described by Ristic, supra, and also obtained from a commercial source (ANAPLAZ vaccine freeze dried powder from Fort Dodge Laboratories, Fort Dodge, Iowa). As a control, non-infected bovine erythrocyte stroma (NBES) was prepared in the same way as AA, except that the starting blood was obtained from an animal determined to be not infected with AM.

Fluorescein isothiocyanate-conjugated goat-derived antihuman gammaglobulin was obtained from a commercial source (Electronucleonics, Inc.). One lot was reactive at very low titer with AM, which was not unexpected because goat-derived antihuman gammaglobulin is derived from pooled human serum which would include serum from SLE-infected persons. The lot with the low AM titer was absorbed before use with 2 mg/ml of AA. In all readings a blank was prepared on every slide (after appropriate coding) to eliminate all possibility of a positive result from the reagents alone.

Blood sera were collected from:
1. Twenty-two patients with a diagnosis of SLE established by renal biopsy or definitive serologic tests,
2. Sixty consecutive sera collected for a serologic test for syphilis and found to be nonreactive,
3. Twenty-seven hospitalized patients with a clinical diagnosis of cirrhosis, and
4. Fifteen hospitalized patients with drug addiction with a proven diagnosis of bacterial endocarditis.

The sera from categories 2, 3 and 4 (102 persons) were considered to be controls.

Serum from each person was applied to a separate glass slide coated with freeze dried Anaplasma antigen. As negative controls, serum was also applied to glass slides coated with freeze dried normal bovine erythrocytes. Fluorescein-conjugated antihuman immunogamma globulin was then applied to all of the slides and the excess was then washed off.

All of the slides were read at the same time without knowledge of their origin or manipulation.

For sera found to be positive (producing fluorescence) in the tests, additional tests were run at higher titers (greater dilutions) until a negative reading was obtained.

A positive result was interpreted as outline or complete fluorescence of the marginal bodies of *Anaplasma marginale* in infected bovine erythrocytes.

Strongly positive readings were obtained on the sera of all twenty-two patients who had previously been diagnosed as SLE patients. The minimum antibody titer on these patients was 20, showing a positive reading when the serum was diluted to 1/20 of its concentration.

Negative, or weakly positive readings were obtained on the sera of most of the 102 controls (59.8% having antibody titers of 5 or less, 69.6% having titers below 20, and only 12.7% having titers above 20.

The titer results are shown in the following table:

TABLE

| Titer | % of SLE Patients* | % of Controls* |
|---|---|---|
| 5 or less | — | 59.8 |
| 10 | — | 9.8 |
| 20 | 13.7 | 17.6 |
| 40 | 18.2 | 2.0 |
| 80 | 22.8 | 5.9 |
| 160 | 22.8 | 2.0 |
| 320 | 9.1 | 1.0 |
| 640 | 4.6 | 1.0 |
| 1280 | 9.1 | 1.0 |
| | 100.3 | 100.1 |

*Sums add up to slightly more than 100.0 because of rounding.

The geometric mean titer for the known SLE patients was 116.0. The geometric mean titer for the persons tested for syphilis and found negative was 11.3, for the cirrhosis patients was 8.0, for the endocarditis patients was 16.7, and for all controls was 10.7.

Gamma globulin levels were determined on some of the sera from each class of controls. Among the persons tested for syphilis and found negative there were no abnormally high gamma globulin levels among the twelve sera tested and the geometric mean level was 12.66 g/100 g protein. Among the cirrhosis patients there were seven out of ten tested who had levels of gamma globulin above the normal range; and the geometric mean gamma globulin level for the ten patients was 24.13 g/100 g protein. Among the endocarditis patients there were six out of seven tested who had levels of gamma globulin above the normal range; and the geometric mean gamma globulin level for the seven patients was 32.10 g/100 g protein. The normal range of gamma globulin for these tests was taken to be 11–22 g/100 g protein.

The invention has been described with respect to its preferred embodiments. It will be understood by those skilled in the art, however, that variations and modifications may be employed without departing from the essence of this invention.

I claim:
1. A method for determining the presence of systemic lupus erythematosus in a patient which comprises contacting blood serum from said patient with anaplasma antigen derived from a vertebrate infected with an organism of the family Anaplasmataceae, and thereafter contacting said antigen with an indicator for human immunoglobulin components and determining the presence of systemic lupus erythematosus by a positive reaction to said indicator.

2. The method of claim 1 wherein said organism is *Anaplasma marginale* (AM).

3. The method of claim 2 wherein vertebrate is a bovine animal.

4. The method of claim 1 wherein said indicator is a goat-derived antihuman gamma globulin conjugated with fluorescein isothiocyanate and determining the presence of systemic lupus erythematosus by the presence of fluorescence in the product obtained by contacting said antigen with said indicator.

5. The method of claim 4 wherein said goat-derived antihuman gamma globulin conjugated with fluorescein isothiocyanate is first absorbed with anaplasma antigen at a low titer.

6. The method of claim 1 wherein said anaplasma antigen is in the form of a smear on a glass plate.

7. The method of claim 6 wherein said smear is dried and preserved in a frozen state.

8. The method of claim 1 wherein said blood serum is diluted to a strength not higher than about 1/20 of its original strength before being contacted with said antigen.

* * * * *

UNITED STATES PATENT AND TRADEMARK OFFICE
CERTIFICATE OF CORRECTION

PATENT NO. : 4,329,331
DATED : May 11, 1982
INVENTOR(S) : Charles A. Kallick

It is certified that error appears in the above-identified patent and that said Letters Patent is hereby corrected as shown below:

On the title page, abstract, line 4, "genus" should read -- family --.

Column 1, line 66, "genus" should read -- family --.

Column 3, line 33, "SLE-infected persons" should read -- goats infected with Anaplasmataceae --.

Signed and Sealed this

Twenty-ninth Day of March 1983

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,329,331
DATED : May 11, 1982
INVENTOR(S) : Charles A. Kallick

It is certified that error appears in the above-identified patent and that said Letters Patent is hereby corrected as shown below:

Column 3, line 33, "SLE-infected persons" should read
--goats infected with Anaplasmataceae--.

Signed and Sealed this

Sixth Day of September 1983

[SEAL]

Attest:

GERALD J. MOSSINGHOFF

Attesting Officer    Commissioner of Patents and Trademarks